United States Patent [19]

Maatta

[11] Patent Number: 5,359,119
[45] Date of Patent: Oct. 25, 1994

[54] HOMOGENEOUS, LOW-TEMPERATURE TRANSITION METAL-MEDIATED SYNTHESIS OF NITRILES

[75] Inventor: Eric A. Maatta, Manhattan, Kans.

[73] Assignee: Kansas State University Research Foundation, Manhattan, Kans.

[21] Appl. No.: 194,411

[22] Filed: Feb. 10, 1994

Related U.S. Application Data

[63] Continuation-in-part of Ser. No. 65,456, May 20, 1993, abandoned, which is a continuation of Ser. No. 914,995, Jul. 16, 1992, abandoned, which is a continuation-in-part of Ser. No. 764,006, Sep. 23, 1991, abandoned.

[51] Int. Cl.⁵ ............................................. C07C 253/00
[52] U.S. Cl. ..................................... 558/308; 558/317
[58] Field of Search ............... 558/317, 308, 323, 329, 558/330

[56] References Cited

PUBLICATIONS

Maatta, et al., J. A. C. S., 110, (1988), pp. 8249–8250.
Maatta et al., J. Chem. Soc., Chem. Communications, Issue 10, (1990), pp. 756–757.
Burrington, et al., Journal of Catalysis, 87, (1984), pp. 363–380.

*Primary Examiner*—Joseph Paul Brust
*Attorney, Agent, or Firm*—Hovey, Williams, Timmons & Collins

[57] ABSTRACT

A low temperature, solution phase process for synthesizing nitriles such as acrylonitrile and benzylnitrile is provided which makes use of a transition metal complex bearing an imido moiety to form a final nitrile corresponding to the moiety. In practice, a solution of a transition metal complex is formed in a non-interfering solvent, and the solution is reacted under time and temperature conditions to form the desired nitrile. The solution may also contain a base such as pyridine.

8 Claims, No Drawings

HOMOGENEOUS, LOW-TEMPERATURE TRANSITION METAL-MEDIATED SYNTHESIS OF NITRILES

RELATED APPLICATION

This is a continuation-in-part of application Ser. No. 08/065,456, filed May 20, 1993 which was a continuation of application Ser. No. 07/914,995, filed Jul. 16, 1992, which is a continuation-in-part of application Ser. No. 07/764,006, filed Sep. 23, 1991, all now abandoned.

BACKGROUND OF THE INVENTION

1. Field of the Invention

The present invention is broadly concerned with an improved, solution phase technique for the synthesis of nitriles such as acrylonitrile and benzonitrile. More particularly, it is concerned with nitrile syntheses wherein a transition metal complex bearing an imido moiety ($R-CH_2-N\equiv$) is reacted in solution under time and temperature conditions to form a nitrile ($R-C\equiv N$) corresponding to the imido moiety.

2. Description of the Prior Art

Current worldwide production of acrylonitrile is approximately 8 billion pounds per year, virtually all of which is polymerized to form polyacrylonitrile used in fabrics, fibers, containers and elastomers. Virtually all commercial acrylonitrile is produced by high temperature, energy-intensive heterogeneous catalysis methods wherein a mixture of hot gases (propylene, ammonia and oxygen) are passed over a metal oxide surface in an extremely exothermic reaction. Such heterogeneous systems are notoriously complex, contain a multitude of different possible active sites, and cannot be analyzed in detail. Moreover, the overall yield of acrylonitrile (based on propylene) is in the range of 65–85%, an inefficiency that is dramatic for such large scale processes. Finally, current industrial techniques produce environmentally noxious acetonitrile and hydrogen cyanide as byproducts.

In Maatta et al. *Am. Chem. Soc.*, 110:8249 (1988), the complex [$CH_2=CH-CH_2-N=WCl_4(THF)$] was reacted only with a stoichiometric amount of a specifically chosen base (butyl lithium) in order to characterize an intermediate species. This stoichiometry prevented the formation of acrylonitrile.

Accordingly, a relatively low temperature, solution phase process free of detrimental byproducts for the production of nitriles would be a decided breakthrough in the art.

SUMMARY OF THE INVENTION

The present invention overcomes the problems outlined above and provides a greatly improved, low energy method of synthesizing nitrile compounds. Broadly speaking, the method of the invention includes the steps of forming a solution of a transition metal complex bearing an imido moiety in a non-interfering solvent. This solution is reacted under time and temperature conditions to form a nitrile ($R-C\equiv N$) corresponding to the imido moiety ($R-CH_2-N$), which nitrile may then be recovered by conventional means.

The imido moieties of the transition metal complexes useful in the context of the present invention have the general formula $R-CH_2-N$ where R represents any desired substituent such as an alkyl or alkenyl group having from about 1–9 carbon atoms or an aryl group (which may itself be substituted); notable substituents R include $CH_2=CH-$ (corresponding to an allylimido moiety) and $C_6H_5$ (corresponding to a benzylimido moiety).

The preferred transition metal complexes useful in the context of the present invention have the general formula.

where, R is selected from the group of alkyl and alkenyl groups having from 1–9 carbon atoms and substituted and unsubstituted aryl groups; e.g., substituted and unsubstituted phenyl groups wherein the substituents may be alkyl or alkenyl groups having from 1–6 carbon atoms, halogens, etc. Substituents M and M' are each one member of and individually selected from the group consisting of Mo, W, and V. Substituents X and X' are each one member of and selected from the group consisting of oxygen, halogen, silicon, and phosphorous atoms and imido and alkoxide groups. Y is one member of and selected from the group consisting of the nitriles, ethers, phosphines and phosphine oxides. Q is a charged counterion for rendering the complex electrically neutral. The subscript a ranges from about 1–40, whereas the sum of b and b' ranges from about 1–40, the sum of c and c' ranges from about 1–40, d ranges from about 0–6, and e ranges from about 0–7. As used herein, the expression "one member of" with reference to the groupings of substituents means that each respective substituent is made up of only one member of the corresponding group, and that possible substituents made up of multiple members of the corresponding group are precluded. For example, in the case of substituents X and X', a hypothetical group including both a phosphorous and silicon atom would be precluded.

A representative transition metal complex found to be useful in the invention is [$CH_2=CH-CH_2-N=WCl_4(THF)$].

As indicated, the solvent employed should be non-interfering, i.e., it should not adversely affect the reaction of the transition metal complex or the ultimate nitrile formation. Generally speaking, the solvent systems employed are non-aqueous, comprising organic solvents. In certain systems, it has been found that the solvent should include or consist essentially of a base. Representative bases include pyridine, the alkylamines, the alkali and alkaline earth hydroxides, and organolithium bases. Where a base is advantageous or required, it is normally present in molar excess relative to the complex.

The reaction conditions found to be useful in the invention are variable depending upon the transition metal complex employed and the solvent system used. Broadly, however, the solution reaction temperature should range from about 0°–250° C., and more preferably from about 20°–150° C. In some cases, the reaction may be carried out for an initial period at essentially room temperature, and thereafter at elevated temperatures. Similarly, reaction times can vary, but typically the solution is reacted for a period of at least about 12 hours, and more preferably from about 12–72 hours. The reactions of the invention are normally carried out at ambient pressures and in an oxygen-free atmosphere.

The production of the most commercially significant nitrile, acrylonitrile, is preferably accomplished by forming a solution including a complex of the formula [$CH_2=CH-CH_2-N=WCl_4(THF)$] and a base (e.g., pyridine), and reacting this solution at a temperature of from about 15°–40° C. (most preferably room temperature) for a time of from about 12–48 hours. Acrylonitrile may then be recovered by any conventional means.

DESCRIPTION OF THE PREFERRED EMBODIMENTS

The following examples illustrate the methods of the present invention. It should be understood that these examples are merely representative of the invention, and should not be construed as a limitation upon the overall scope thereof.

EXAMPLE I—BENZONITRILE SYNTHESIS

The synthesis included the steps of reacting available precursor reagents to form a transition metal complex, and reacting the complex with a pyridine base to form benzonitrile. Under a nitrogen atmosphere, a 250 mL two-necked flask was charged with 0.50 g (1.31 mmol) of MoCl$_4$(THF)$_2$ prepared according to the method of Allen, et al., *J. Chem. Soc.*, 1636 (1965). The flask was fitted with a reflux condenser and an inlet valve. CDCl$_3$ (7 mL) was added to partially dissolve the solid. Benzyl azide, C$_6$H$_5$—CH$_2$—N$_3$ (0.175 g; 1.31 mmol) was then introduced to the suspension, and the mixture was stirred at ambient temperature (ca, 23° C.) for 1 h, during which time a dark red solution formed. The CDCl$_3$ solvent was then removed by evacuation, leaving a dark brownish residue including the desired transition metal complex. Subsequently, 6 mL of deuterated pyridine (py-D$_5$) was added to the residue under a nitrogen atmosphere. A bright red solution formed immediately and was stirred at room temperature for 24 h, whereupon the solution was heated to 115° C. and refluxed for an additional 45 h. The reaction flask was then placed in a 100° C, water bath and all volatile material was collected in a liquid nitrogen filled trap under vacuum.

The collected liquid was analyzed by $^1$H NMR spectroscopy as follows. The material was placed in an NMR sample tube and a portion of CH$_2$Br$_2$ (0.0793 g; 4.56×10$^{-4}$ mol) was added to the tube as an internal standard for quantification. The $^1$H NMR spectrum indicated the presence of benzonitrile (C$_6$H$_5$—CN), which was confirmed by comparison to the spectrum of an authentic sample dissolved in pyridine-D$_5$. Integration of the resonances due to CH$_2$Br$_2$ and C$_6$H$_5$—CN, and comparison of their relative areas, indicated that 3.41×10$^{-4}$ mol of benzonitrile was formed.

The results indicated that the transition metal complex had the formula (C$_6$H$_5$—CH$_2$—N)MoCl$_4$(THF) where, in terms of the general formula, R is C$_6$H$_5$, a is 1, M is molybdenum, b is 1, b' is zero, X is chlorine, c is 4, c' is zero, Y is tetrahydrofuran ("THF"), d is 1, and e is zero.

EXAMPLE II—BENZONITRILE SYNTHESIS

A portion of [(n—C$_4$H$_9$)$_4$N]$_2$[Mo$_6$O$_{19}$](1.86 g; 1.36×10$^{-3}$ mol), prepared according to the method described by Fuchs, et al., *Zeitschrift fur Naturforschung*, 23B, 1380 (1968), was suspended in 15 mL of CDCl$_3$, and N-benzyltriphenylphosphinimine (Ph$_3$P=NCH$_2$C$_6$H$_5$; 0.50 g; 1.35 mmol) was added to the suspension under a nitrogen atmosphere. The phosphinimine (C$_6$H$_5$—CH$_2$—N=PPh$_3$) was employed as the imido ligand delivery agent in this example. The temperature of the system was maintained at 60° C. for 40 h while the reaction mixture was stirred. After that time, the reaction flask was placed in a water bath at 50° C. and the volatile liquids were collected in a liquid nitrogen-cooled trap under vacuum. The total weight of the collected liquid was found to be 26.8584 g.

The collected liquid was analyzed by NMR spectroscopy as follows. A portion (1.3725 g) of the liquid was placed in an NMR tube and CH$_2$Br$_2$ (0.0090 g; 5.18×10$^{-5}$ mol) was introduced as an internal quantification standard. The $^1$H NMR spectrum indicated the presence of benzonitrile, which was confirmed by comparison to the spectrum of an authentic sample dissolved in CDCl$_3$. Integration of the resonances due to benzonitrile and CH$_2$Br$_2$, and comparison of their relative areas indicated that the total amount of benzonitrile produced was 7.08×10$^{-5}$ mol.

The results indicated that the transition metal complex had the formula

[(C$_6$H$_5$—CH$_2$—N)Mo$_6$O$_{18}$][(n—C$_4$H$_9$)$_4$N]$_2$ where, in terms of the general formula, R is C$_6$H$_5$, a is 1, M is molybdenum, b is 6, b' is zero, X is oxygen, c is 18, d is zero, Q is (n—C$_4$H$_9$)$_4$N, and e is 2.

EXAMPLE III—ACRYLONITRILE SYNTHESIS

Under a nitrogen atmosphere, a 250 mL two-necked flask was charged with 0.50 g (1.31 mmol) of MoCl$_4$(THF)$_2$ prepared according to the method of Allen, et al., *J. Chem. Soc.*, 1636 (1965). The flask was fitted with two inlet valves. CDCl$_3$ (10 mL) was added to partially dissolve the solid. Allyl azide, CH$_2$=CH—CH$_2$—N$_3$, (0.109 g; 1.31 mmol) was then introduced to the suspension, and the mixture was stirred at ambient temperature (ca. 23° C.) for 1 h., during which time a dark red solution formed. The CDCl$_3$ solvent was then removed by evacuation, leaving an orange residue. To this residue was added 5 mL of deuterated pyridine (py-D$_5$), under a nitrogen atmosphere. A brown-purple solution formed immediately and was stirred at room temperature for 24 h. The reaction flask was then placed in a 80° C. water bath and all volatile material was collected in a liquid nitrogen filled trap under vacuum.

The collected liquid was analyzed by $^1$H NMR spectroscopy as follows. The material was placed in an NMR sample tube and a portion of CH$_2$Br$_2$ (0.0123 g; 7.08×10$^{-5}$ mol) was added to the tube as an internal standard for quantification. The $^1$H NMR spectrum indicated the presence of acrylonitrile (CH$_2$=CH—CN), which was confirmed by comparison to the spectrum of an authentic sample dissolved in pyridine-D$_5$. Integration of the resonances due to CH$_2$Br$_2$ and CH$_2$=CH—CN, and comparison of their relative areas, indicated that 2.12×10$^{-5}$ mol of acrylonitrile was formed.

The results indicated that the transition metal complex formed prior to the addition of the pyridine base had the formula

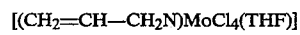
[(CH$_2$=CH—CH$_2$N)MoCl$_4$(THF)]

where, in terms of the general formula, R is CH$_2$=CH, a is 1, M is molybdenum, b is 1, b' is zero, X is chlorine, c is 4, c' is zero, y is THF, d is 1, and e is zero.

EXAMPLE IV—ACRYLONITRILE SYNTHESIS

The complex [(CH$_2$=CH—CH$_2$—N)WCl$_4$(THF)] is generated in situ by the addition of CH$_2$=CH—CH- 2—NH—SiMe$_3$ (0.165 g; 1.25×10$^{-3}$ mole) to a solution of WCl$_6$ (0.5 g; 1.25×10$^{-3}$ mole) in ca. 10 mL of C$_6$D$_6$. After stirring for 10 minutes at room temperature, one equivalent of tetrahydrofuran (THF; 0.090 g; 1.25×10$^{-3}$ mole) is added to the mixture resulting in the formation of a bright red solution of the allylimido complex. 2 mL of pyridine-d$_5$ is added to this solution, resulting in the immediate precipitation of a brown-pink product. The pale solution was decanted away and 1 mL of pyridine-d$_5$ was added to dissolve the precipitate. The resulting solution was stirred at room temperature for 20 hours. After that time, the volatile liquids were collected in a liquid nitrogen-cooled trap under vacuum. A known amount of CH$_2$Br$_2$ is added to the distillate as an internal quantification standard and the mixture is placed in an NMR tube for analysis by $^1$H NMR spectroscopy. The $^1$H NMR spectrum reveals the presence of acrylonitrile (CH$_2$=CH—C≡N; 7.5×10$^{-6}$ mole; 0.6% yield) and propionitrile (CH$_3$—CH$_2$—C≡N; 2.5×10$^{-5}$ mole; 2.0% yield), whose relative amounts were determined by comparison of the integrated areas of their resonances to that of the internal standard.

The transition metal complex

[(CH$_2$=CH—CH$_2$—N)WCl$_4$(THF)]

relates to the generalized formula of the invention, where R is CH$_2$=CH, a is 1, M is tungsten, b is 1, b' is zero, X is chlorine, c is 4, c' is zero, y is THF, d is 1, and e is zero.

In this example, two nitriles were formed, acrylonitrile and propionitrile; the latter may result from a subsequent reaction of the acrylonitrile product. The low yield is obtained after a relatively short reaction time at relatively low temperatures. Higher yields are expected by extending the reaction time and performing the reaction at higher temperatures.

It will thus be seen that the present invention provides a greatly improved process for the synthesis of commercially valuable nitriles. Of particular note is the fact that the methods of the invention are carried out in solution, thereby offering the distinct advantage of permitting detailed monitoring by conventional spectroscopic means (such as nuclear magnetic resonance studies). The present methods also offer the potential for facile modifications by simple variations in the nature of the groups bound to the active transition metal sites of the complexes.

Table I below lists a number of exemplary transition metal complexes useful in the syntheses of nitriles of the formula R—C≡N, where R is defined in the Table, along with the other substituents and subscripts corresponding to the general formula. These complexes may be prepared according to the known methods described above, from known polyoxometalates that are used as precursors to the complexes, such as the polyoxometalates that are prepared as described in Filowitz et al, $^{17}$O Nuclear Magnetic Resonance Spectroscopy of Polyoxometalates. 1. Sensitivity and Resolution, *Inorganic Chemistry*, 18: 93 (1979), which is hereby incorporated by reference. These complexes may then be converted to the corresponding nitriles using the time and temperature reaction conditions described previously.

TABLE I

EXEMPLARY TRANSITION METAL COMPLEXES ACCORDING TO THE GENERAL FORMULA
[R—CH$_2$—N)$_a$M$_b$M'$_{b'}$X$_c$X'$_{c'}$Y$_d$][Q]$_e$

| Transition Metal Complex | R | a | M | b | M' | b' | X | c |
|---|---|---|---|---|---|---|---|---|
| [(C$_6$H$_5$—CH$_2$—N)VMo$_5$O$_{18}$][(n-C$_4$H$_9$)$_4$N]$_3$ | C$_6$H$_5$ | 1 | V | 1 | Mo | 5 | O | 18 |
| [(CH$_2$=CH—CH$_2$—N)$_2$Mo$_{12}$O$_{38}$P][(n-C$_4$H$_9$)$_4$N]$_3$ | CH$_2$=CH | 2 | Mo | 12 | | 0 | O | 38 |
| [(C$_6$H$_5$—CH$_2$—N)$_6$Mo$_2$O][(n-C$_4$H$_9$)$_4$N]$_2$ | C$_6$H$_5$ | 6 | Mo | 2 | | 0 | O | 1 |
| [(CH$_3$—CH$_2$—N)Mo$_6$O$_{18}$][(n-C$_4$H$_9$)$_4$N]$_2$ | CH$_3$ | 1 | Mo | 6 | | 0 | O | 18 |
| [(CH$_3$(CH$_2$)$_8$—CH$_2$—N)W$_6$O$_{18}$][(n-C$_4$H$_9$)$_4$N]$_2$ | CH$_3$(CH$_2$)$_8$ | 1 | W | 6 | | 0 | O | 18 |
| [(m-(CH$_3$)—(C$_6$H$_4$)—CH$_2$—N)VW$_5$O$_{18}$][(n-C$_4$H$_9$)$_4$N]$_2$ | m-(CH$_3$)—(C$_6$H$_4$) | 1 | V | 1 | W | 5 | O | 18 |
| [(t-(CH$_3$)$_3$C—CH$_2$—N)W$_{12}$O$_{39}$Si][(n-C$_4$H$_9$)$_4$N]$_4$ | t-(CH$_3$)$_3$C | 1 | W | 12 | | 0 | O | 39 |
| [(C$_6$H$_5$—CH$_2$—N)MoCl$_3$(OCH$_3$)(CH$_3$C≡N)] | C$_6$H$_5$ | 1 | Mo | 1 | | 0 | Cl | 3 |
| [(C$_6$H$_5$—CH$_2$—N)MoCl$_3$(OCH$_3$)(P(C$_6$H$_5$)$_3$)] | C$_6$H$_5$ | 1 | Mo | 1 | | 0 | Cl | 3 |
| [(C$_6$H$_5$—CH$_2$—N)MoCl$_3$(OCH$_3$)(O=P(C$_6$H$_5$)$_3$)] | C$_6$H$_5$ | 1 | Mo | 1 | | 0 | Cl | 3 |
| [(C$_6$H$_5$—CH$_2$—N)MoCl$_3$(OCH$_3$)(THF)] | C$_6$H$_5$ | 1 | Mo | 1 | | 0 | Cl | 3 |
| [(CH$_2$=CH—CH$_2$—N)$_{20}$Mo$_{12}$O$_{20}$P][(n-C$_4$H$_9$)$_4$N]$_3$ | CH$_2$=CH | 20 | Mo | 12 | | 0 | O | 20 |
| [(CH$_3$—CH$_2$—N)Mo$_6$O$_{17}$(NC$_6$H$_5$)][(n-C$_4$H$_9$)$_4$N]$_2$ | CH$_3$ | 1 | Mo | 6 | | 0 | O | 17 |

| Transition Metal Complex | X' | c' | Y | d | Q | e |
|---|---|---|---|---|---|---|
| [(C$_6$H$_5$—CH$_2$—N)VMo$_5$O$_{18}$][(n-C$_4$H$_9$)$_4$N]$_3$ | | 0 | | 0 | [(n-C$_4$H$_9$)$_4$N] | 3 |
| [(CH$_2$=CH—CH$_2$—N)$_2$Mo$_{12}$O$_{38}$P][(n-C$_4$H$_9$)$_4$N]$_3$ | P | 1 | | 0 | [(n-C$_4$H$_9$)$_4$N] | 3 |
| [(C$_6$H$_5$—CH$_2$—N)$_6$Mo$_2$O][(n-C$_4$H$_9$)$_4$N]$_2$ | | 0 | | 0 | [(n-C$_4$H$_9$)$_4$N] | 2 |
| [(CH$_3$—CH$_2$—N)Mo$_6$O$_{18}$][(n-C$_4$H$_9$)$_4$N]$_2$ | | 0 | | 0 | [(n-C$_4$H$_9$)$_4$N] | 2 |
| [(CH$_3$(CH$_2$)$_8$—CH$_2$—N)W$_6$O$_{18}$][(n-C$_4$H$_9$)$_4$N]$_2$ | | 0 | | 0 | [(n-C$_4$H$_9$)$_4$N] | 2 |
| [(m-(CH$_3$)—(C$_6$H$_4$)—CH$_2$—N)VW$_5$O$_{18}$][(n-C$_4$H$_9$)$_4$N]$_2$ | | 0 | | 0 | [(n-C$_4$H$_9$)$_4$N] | 3 |
| [(t-(CH$_3$)$_3$C—CH$_2$—N)W$_{12}$O$_{39}$Si][(n-C$_4$H$_9$)$_4$N]$_4$ | Si | 1 | | 0 | [(n-C$_4$H$_9$)$_4$N] | 4 |
| [(C$_6$H$_5$—CH$_2$—N)MoCl$_3$(OCH$_3$)(CH$_3$C≡N)] | OCH$_3$ | 1 | CH$_3$C≡N | 1 | | 0 |
| [(C$_6$H$_5$—CH$_2$—N)MoCl$_3$(OCH$_3$)(P(C$_6$H$_5$)$_3$)] | OCH$_3$ | 1 | P(C$_6$H$_5$)$_3$ | 1 | | 0 |
| [(C$_6$H$_5$—CH$_2$—N)MoCl$_3$(OCH$_3$)(O=P(C$_6$H$_5$)$_3$)] | OCH$_3$ | 1 | O=P(C$_6$H$_5$)$_3$ | 1 | | 0 |
| [(C$_6$H$_5$—CH$_2$—N)MoCl$_3$(OCH$_3$)(THF)] | OCH$_3$ | 1 | THF | 1 | | 0 |
| [(CH$_2$=CH—CH$_2$—N)$_{20}$Mo$_{12}$O$_{20}$P][(n-C$_4$H$_9$)$_4$N]$_3$ | P | 1 | | 0 | [(n-C$_4$H$_9$)$_4$N] | 3 |
| [(CH$_3$—CH$_2$—N)Mo$_6$O$_{17}$(NC$_6$H$_5$)][(n-C$_4$H$_9$)$_4$N]$_2$ | NC$_6$H$_5$ | 1 | | 0 | [(n-C$_4$H$_9$)$_4$N] | 2 |

I claim:

1. A method of synthesizing nitrile compounds comprising the steps of:

forming a solution of a transition metal complex bearing an imido moiety in a non-interferring solvent, said complex having the general formula:

[(R—CH$_2$—N)$_a$M$_b$M'$_{b'}$X$_c$X'$_{c'}$Y$_d$][Q]$_e$ where R is selected from the group consisting of alkyl and alkenyl groups having from 1 to 9 carbon atoms and substituted and unsubstituted aryl groups, M and M' are each one member of individually selected from the group consisting of Mo, W and V, X and X' are each one member of and selected from the group consisting of oxygen, halogen, silicon and phosphorous atoms and imido and alkoxide groups, Y is one member of and selected from the group consisting of the nitriles, ethers, phosphines and phosphine oxides, Q is a charged counterion, a ranges from about 1 to 40, the sum of b and b' ranges from about 1 to 40, the sum of c and c' ranges from about 1 to 40, d ranges from about 0 to 6, and e ranges from about 0 to 7;

reacting said solution at a temperature of from about 0°–250° C. for a period of at least about 12 hours to form a nitrile having the general formula R—C≡N, where R is defined above; and recovering said nitrile.

2. The method of claim 1, said reaction period being from about 12–72 hours.

3. The method of claim 1, R being selected from the group consisting of $CH_2$=CH— and $C_6H_5$— groups.

4. The method of claim 1, said complex being [$CH_2$=CH—$CH_2$—N=$WCl_4$(THF)].

5. The method of claim 1, said solvent including a base.

6. The method of claim 5, wherein said base is selected from the group consisting of pyridine, the alkylamines, the alkali and alkaline earth hydroxides, and organolithium bases.

7. A method of synthesizing acrylonitrile, comprising the steps of:

forming a solution including a transition metal complex having the formula [$CH_2$=CH—$CH_2$—N=$WCl_4$(THF)] and a base; and reacting said solution at a temperature of from about 15°–40° C. for a period of from about 12–48 hours to form acrylonitrile.

8. The method of claim 7, said base comprising pyridine.

* * * * *